United States Patent [19]

Buck

[11] Patent Number: 5,104,793
[45] Date of Patent: Apr. 14, 1992

[54] METHOD FOR DETERMINING AN ANALYTE IN A LIQUID SAMPLE USING A ZONED TEST DEVICE AND AN INHIBITOR FOR A LABEL USED IN SAID METHOD

[75] Inventor: Harvey Buck, Indianapolis, Ind.

[73] Assignee: Boehringer Mannheim Corporation, Indianapolis, Ind.

[21] Appl. No.: 156,168

[22] Filed: Feb. 16, 1988

[51] Int. Cl.⁵ ................ G01N 33/543; G01N 33/558
[52] U.S. Cl. .................... 435/7.92; 422/55; 422/69; 435/7.94; 435/963; 435/970; 435/971; 436/501; 436/512; 436/514; 436/578; 436/548; 436/800; 436/810
[58] Field of Search ........... 435/7, 805, 810, 7.92, 435/7.94, 963, 970, 971; 436/512, 514, 518, 548, 530, 800, 808, 810; 422/56-58, 55, 69

[56] References Cited

U.S. PATENT DOCUMENTS

| | | | |
|---|---|---|---|
| 4,144,306 | 3/1979 | Figueras | 422/56 |
| 4,208,479 | 6/1980 | Zuk et al. | 436/512 |
| 4,391,904 | 7/1983 | Litman et al. | 436/536 |
| 4,435,504 | 3/1984 | Zuk et al. | 436/530 |
| 4,582,792 | 4/1986 | Kasahara et al. | 436/523 |
| 4,690,907 | 9/1987 | Hibino et al. | 436/515 |
| 4,861,711 | 8/1989 | Friesen et al. | 436/514 |

FOREIGN PATENT DOCUMENTS 0202081 11/1986 European Pat. Off. .

Primary Examiner—David Saunders
Attorney, Agent, or Firm—Felfe & Lynch

[57] ABSTRACT

The invention relates to a heterogeneous immunoassay which is carried out using a multizoned test device. In particular, the invention involves the use of an inhibitor of a label which is used in the assay. The label which may be an enzyme, is attached to a receptor such as an antibody. The inhibitor is not acted upon by the label, but must be removed in order for a signal to be produced. Also described are test strips which can be used for the assay.

24 Claims, 2 Drawing Sheets

METHOD FOR DETERMINING AN ANALYTE IN A LIQUID SAMPLE USING A ZONED TEST DEVICE AND AN INHIBITOR FOR A LABEL USED IN SAID METHOD

FIELD OF THE INVENTION

This invention relates to a heterogeneous assay for determining an analyte in a sample, and an apparatus adapted for use in the assay.

BACKGROUND AND PRIOR ART

Heterogeneous assays, in general, involve determination of analytes in samples via a phase change which occurs at some time during the assay run. In a preferred form of assay, a test apparatus, such as a bibulous paper or film based strip, is contacted by the sample to be assayed. The test strip contains a component which interacts in some way with the analyte in the sample, if the analyte is present. As the sample is fluid, it diffuses or passes through the test apparatus, carrying with it any of the analyte, component, and any product resulting from interaction between analyte and component.

Usually, the interaction of analyte and component leads to formation of a reaction product, frequently a complex of analyte and component. The component carries some signal generating means, or label, which allows one to identify and/or to quantify it. The task of the investigator is to determine if the component has complexed to analyte, and/or how much has complexed. This is accomplished by measuring the label.

One fact of assays involving labeled components is that the label is carried by the labeled component regardless of whether it is bound or complexed to analyte. It therefore becomes imperative to have some way of discriminating complexed label from uncomplexed material.

This is achieved in heterogeneous assays by providing a solid phase bound moiety which discriminates between complexed and uncomplexed labeled components. The solid phase bound moiety permits separation of phase (hence the term "heterogeneous"), and identification and quantification of complexed and uncomplexed labeled component.

Various forms of heterogeneous assays will be familiar to the skilled artisan, such as immunoenzymometric assays, which involve formation of complexes between analyte and labeled component, where the complex remains in solution and the uncomplexed label is removed from solution via a solid phase bound reaction partner; so-called "sandwich assays", where a binding partner which is labeled, complexes with the analyte followed by contact with an immobilized moiety which binds to the analyte, forming a sandwich and leaving uncomplexed label in the liquid phase. These two general examples are certainly not exhaustive of the various forms of assays which can be performed.

Many materials are available as the choice of label. One particularly preferred class of labels is enzymes. When an enzyme is used as the label, the identification of complex involves contacting the label, once complexes have formed, with a substrate which reacts with the enzyme to give a detectable signal. Frequently, although not exclusively, the signal is visually determinable, such as the formation of a color or a color change.

While the enzyme label type of assay is quite useful, there are problems with it. One serious problem, which is now discussed, is the problem addressed by this invention.

Generally, the substrate with which the enzyme label reacts is incorporated into the test apparatus together with the label. While these are usually incorporated in the device at different points, a test device is usually absorbent over its entire reactive surface, as it must be for the various components of the test system to be brought together in functional relationships. If the substrate is brought into contact with the labeled component before the desired reaction takes place, the detectable signal is generated at an inappropriate time. When this happens, the test results' accuracy cannot be guaranteed, and, at times, the results cannot even be determined at all. While controls can be run to give baseline or zero values, it must be understood that in practice, the number of heterogeneous assays which are run over any given period is staggering. Performing a control run for each of these thus becomes a theoretical possibility, but a practical impossibility. Surprisingly, the art shows that little attention has been paid to this particular problem. Calenoff, et al., U.S. Pat. No. 4,528,267, teach inhibition of reactions between IgE and allergens, and Monji, et al., U.S. Pat. No. 4,323,647 teach the general principle that there are competitive and non-competitive inhibitors for enzymes, as well as an assay which involves the use of an antibody as an inhibitor of a complex of antigen and enzyme. In this system, one is determining an antigen in a sample. The labeled antigen is identical to that being determined, and the antibody binds to both labeled antigen and sample antigen. Labeled and unlabeled antigen compete for antibody. That portion of labeled antigen which does not bind to antibody is free to bind to solid phase bound substrate, while antibody bound antigen-enzyme complex is sterically hindered from doing the same. By this rather involved process, one determines the amount of antigen present in the sample. It will be understood, that this system could not be used to address the problem referred to supra, because the enzyme label is still free to react with substrate, should premature contact take place.

European Patent Application 202 081 teaches use of an alternate substrate to delay reaction of the enzyme in the test device with the substrate which will be used to form the detectable moiety. The alternate substrate, however, is chosen so that it is acted upon by the enzyme: expressed another way, the inhibition of the enzyme lasts only as long as the substrate itself remains undigested. This differs from a true inhibitor, which will impede the enzyme until actually removed.

Hence it is an object of the invention to provide a method for inhibiting formation of a detectable signal produced by interaction of enzyme label and substrate until the desired reaction between analyte and receptor occurs, wherein the removal of the inhibitor lies in the control of the investigator.

It is further object of the invention to provide a test apparatus which can be used in connection with the method outlined above.

It is still another object of the invention to provide a reagent or kit which can be used to prepare a device for determination of an analyte, utilizing the method described above.

How these and other objects of the invention are accomplished will be seen from the disclosure which follows.

DETAILED DESCRIPTION OF PREFERRED EMBODIMENTS

Figure 1:
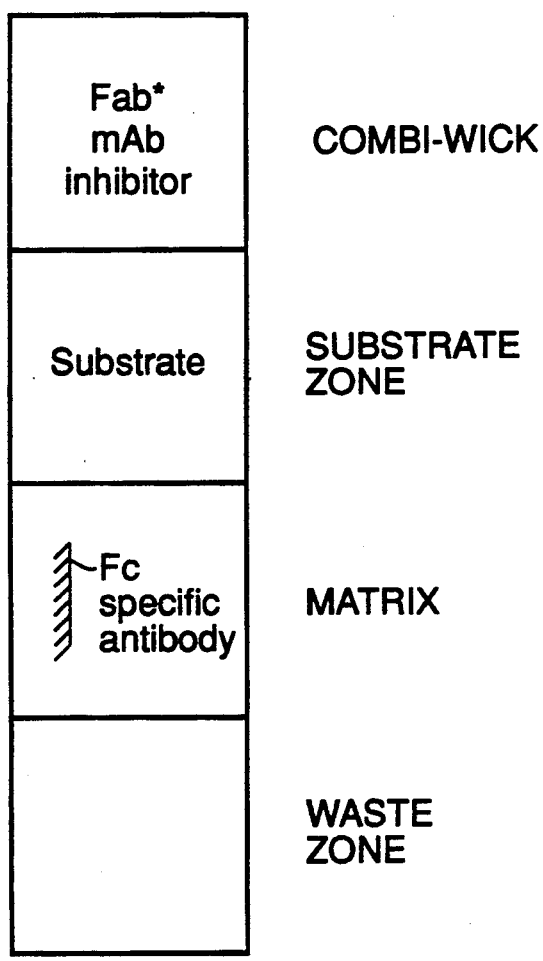
FIG. 1 shows a test device of the type described in Example 1.
Figure 2:
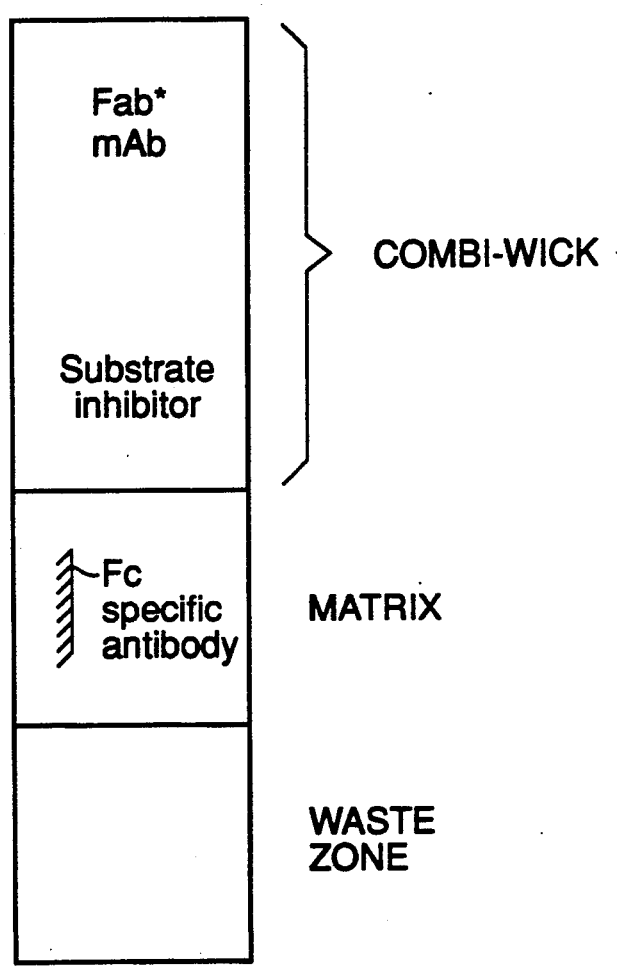
FIG. 2 shows a test device of the type described in Example 2.

The following disclosure teaches a method for determining an analyte in a sample, where the analyte contacts at least one receptor which carries a label and an inhibitor which impedes the detectability of the label. The inhibitor impedes interaction of the label and any substance with which it may interact until the formation of a complex between the analyte and the label carrying receptor occurs. The inhibitor is then removed by treating the complex in some fashion. Frequently, this takes the form of washing the complexes with a solution, such as a run buffer, deionized water, and so forth, which removes the inhibitor, thus permitting the actual substrate to react therewith. As will be seen, infra, the mechanism underlying this method allows one to have the substrate present even while complex formation is occurring, although it will be understood that the substrate may also be added after the inhibitor is removed.

In the examples which now follow, a sandwich immunoassay format was used, although it will be understood by those skilled in the art that the mechanism involved is applicable to any type of assay, such as immunoenzymometric, competitive, displacement and other forms of assays. In a competitive assay, e.g., the sample is contacted to a sample of labeled analyte or labeled analyte analogue, and a receptor such as an antibody, monoclonal antibody, etc., which binds to the labeled component as well as to the sample analyte. Competition for the receptor ensues, and measurement for determining the sample analyte involves measuring the amount of label bound to receptor or in liquid phase, once the inhibitor is removed. The displacement type of assay involves displacing labeled analyte or analyte analogue which was already bound to a receptor prior to contact with sample analyte. Again, measurement proceeds as indicated supra. Similarly, the decision to label an antibody, monoclonal antibody, or antibody fragment, such as a Fab or F(ab)$_2$ fragment rather than another species, such as an antigen, is one left to the skilled artisan.

The examples describe determination of the hormone human chorionic gonadotropin (hCG), in sandwich assay format. An antibody specific to hCG, and coupled to the enzyme beta galactosidase was used throughout the examples.

The enzyme substrate used in the examples is 1-Naphthol-$\beta$-D-galactopyranoside, which is acted on by $\beta$-galactosidase to release 1-Naphthol, which may be oxidized by a peroxidase in the presence of a peroxide source to generate a blue dye.

EXAMPLE 1

A piece of 4210 paper (Firma Kalff) was cut into a strip 2.6 cm long and 0.6 cm wide. One end was impregnated with 100 $\mu$l PBS buffer (pH 7.0, 1% BSA, 0.1% tween-20), and its center portion was impregnated with 7.5 $\mu$l of a solution containing 20 U/mL of a conjugate of an Fab portion of a monoclonal antibody against hCG and beta-galactosidase, 100 $\mu$g/mL of a monoclonal antibody against the beta chain of hCG, and 7.5 mg/mL of p-aminobenzyl-1-thio-$\beta$-D-galactopyranoside, a beta-galactosidase inhibitor. The end of the strip opposite the buffer-impregnated end was impregnated with 10 $\mu$l of an aqueous solution of 5% polyvinyl alcohol. This portion was termed the "combi-wick".

Another piece of 4210 paper was cut to 2.6 cm by 0.6 cm, and 20 $\mu$l of a 40 mg/mL solution of 1-Naphthol-$\beta$-D-galactopyranoside in DMSO was mixed with 20 ul of a 24% solution of polyvinyl alcohol in water. This mixture was applied to the middle of the paper strip. This strip was termed the "substrate wick". A piece of Schleicher and Schuell 3512 paper was activated with cyanogen bromide, and sheep antibodies to the Fc portion of mouse antibodies were fixed thereto.

To conduct the sample analysis, 0.5 mL of sample was added to a glass tube. This was diluted with 0.5 mL of a solution of 4 mMol/L sodium perborate and 10 mg/L of horseradish peroxidase in phosphate buffer, pH 7.0. The end of the test strip was placed in the liquid and the liquid was allowed to migrate up the strip. After 10 minutes, the strip was removed from the tube and the 3512 paper containing sheep antibodies was inspected for color formation.

When no inhibitor is present in the combi-wick, a blue color forms on the observation zone shortly after the sample passes through the substrate wick and onto the 3512 matrix. When inhibitor is present in the combi-wick, there is no color formed on the 3512 matrix until the solution front has migrated far into the waste zone. Then blue color forms in the presence of 1000 mIU/mL hCG in the sample, and does not if no hCG is present in the sample. Thus, observing the matrix zone and waste zone at 15 minutes after sample application yields:

| Inhibitor | hCG | Matrix Color | 15 Min. Observation Waste Color |
|---|---|---|---|
| 0 | 0 | Blue | Blue |
| 0 | 1000 | Blue | Blue |
| 7.5 mg/mL | 0 | White | Blue |
| 7.5 mg/mL | 1000 | Blue | Blue |

The inhibitor clearly prevents color formation until the heterogeneous separation step of the assay is complete and the excess conjugate and the inhibitor are washed into the waste zone by the continued flow of sample.

EXAMPLE 2

A combi-wick was constructed as above, but no p-amino-benzyl-1-thio-$\beta$-D-galactopyranoside was included. A substrate wick was constructed as above, but 7.5 $\mu$l of a 7.5 mg/mL solution of p-aminobenzyl-1-thio-$\mu$-D-galactopyranoside was applied next to the portion containing the substrate and the PVA. This strip was assembled as above, with the part containing the inhibitor closest to the 3512 matrix. The test strips was placed in sample tubes prepared as above and the results observed at 15 minutes.

| hCG | Matrix Color | Waste Color |
|---|---|---|
| 0 | White | Blue |
| 1000 | Blue | Blue |

As above, the inhibitor has prevented color formation on the observation area until the excess label has been washed into the waste area.

The foregoing examples show that a non-reactive inhibitor can prevent premature reaction between enzyme and substrate in a test system, so as to prevent unwanted background color formation. Using a system which incorporates an inhibitor ensures that the integrity of the test results is more certain.

The examples also demonstrate that the placement of the inhibitor can vary in the testing device. In most test strips, there are at least three distinguishable "areas" or "zones", viz., a first zone which is adapted for reception of a sample; a second zone which contains the moiety effecting solid phase separation, and the waste zone. In these examples, the first zone has contained the "combiwick" and "substrate wick", and it has been shown that the inhibitor may be placed in either of these. It is to be understood that the so-called "combi-wick" is the region containing the receptor or receptors which bind to the analyte, and of course, the reactive label. The substrate wick, although a separate physical entity in the test devices used here, need not be physically separate, and the "substrate zone" may merge with any part of the test strip device. For example, the substrate zone and the second zone or "matrix" as it is referred to herein, may constitute a single structure.

The examples utilized a quarternary sandwich structure for signal generation. The skilled artisan will recognize, however, that the choice of assay may vary, depending upon many factors, such as availability of the reagents, the multiepitopic nature of the analyte being determined and so forth. Similarly, the label itself can vary. Horseradish peroxidase, and other peroxidases, are all usable in the system, as are enzymes such as glucose oxidase, uricase, catalase, alkaline phosphatase, amylase, and so forth. Different indicator molecules, and inhibitors may also be used.

The invention also embraces kits for preparing test strips and devices of the type exemplified herein. The kits contain a receptor which will bind to the analyte being determined, such as an antibody, monoclonal antibody, reactive antibody fragment, and so forth, a reactant, such as an indicator which reacts with the antibody to form a signal, and an inhibitor which impedes the signal detection.

It will be understood by the skilled artisan, of course, that to get any signal, the inhibitor must be displaced from its interaction with the label. This happens by the action of the substrate or reactant itself, which can, in appropriate concentration, compete with and "push" the inhibitor from the label. It may also be accomplished by washing or otherwise treating the device once the inhibitor and label interact, but before the substrate is added. The washing step is particularly useful when the device is configured such that inhibitor reaches the label first, and a delaying structure is incorporated into the device to slow down passage of the reactant or substrate and interaction with the label.

It will be understood that the specification and examples are illustrative but not limitative of the present invention and that other embodiments within the spirit and scope of the invention will suggest themselves to those skilled in the art.

I claim:

1. Method for determining an analyte in a liquid sample, comprising:
   (i) contacting a liquid sample to a zoned device containing first, second, and third zones, wherein said first and second zones are in fluid contact with each other and said second and third zones are in fluid contact with each other, to permit flow of liquid sample from said first zone into said second zone and from said second zone into said third zone, wherein
   (ii) said first zone contains at least one non-solid phase bound, label carrying receptor which specifically binds to said analyte to form a complex of receptor and analyte in a liquid phase,
   (iii) said second zone contains a non-solid phase bound inhibitor for the label of said labelled receptor, wherein said inhibitor is not acted upon by said label and directly inhibits said label from forming a detectable signal when said liquid phase containing complexes of receptor and analyte flows from said first zone and into said second zone,
   (iv) said third zone contains a solid phase bound, unlabelled receptor which specifically binds to complexes of analyte and labelled receptor but not to said inhibitor when liquid containing (a) complexes of analyte and labelled receptor and (b) inhibitor flow therein from said second zone, wherein said contacting is carried out under conditions favoring binding of said complex and said solid phase receptor,
   (v) removing said inhibitor from said third zone, and
   (vi) determining a detectable signal produced in said third zone by said label in said complex as a determination of said analyte.

2. Method of claim 1, wherein said receptor is an antibody or fragment thereof.

3. Method of claim 1, wherein said receptor is a monoclonal antibody or fragment thereof.

4. Method of claim 1, wherein said label is an enzyme.

5. Method of claim 4, wherein said inhibitor is an analogue of a substrate for said enzyme.

6. Method of claim 1, wherein said label is a fluorescent label.

7. Method of claim 6, wherein said inhibitor is a quenching molecule for said label.

8. Method of claim 1, wherein treating said complex to remove said inhibitor comprises washing said complex with a fluid.

9. Method of claim 1 further comprising contacting said complex with a substance which competes with said inhibitor for a binding site on said label in an amount sufficient to displace at least a portion of said inhibitor.

10. Method of claim 1, wherein said first zone further comprises a second, non-solid phase bound unlabelled receptor which specifically binds to said analyte but not said labelled receptor, and said solid phase bound, unlabelled receptor specifically binds to said second, non solid phase bound, unlabelled receptor.

11. Method for determining an analyte in a liquid sample comprising:
   (i) contacting a liquid sample to a zoned device containing a first and second zone which are in fluid contact with each other so as to permit flow of liquid from said first zone to said second zone, wherein
   (ii) said first zone contains both (a) at least one non-solid phase bound, labelled receptor which specifically binds to said analyte to form a complex of receptor and analyte upon contact with analyte containing liquid and (b) a non-solid phase bound inhibitor for the label of said labelled receptor, wherein said inhibitor is not acted upon by said label and directly inhibits said label from providing a detectable signal, (iii) said second zone contains a solid phase bound, unlabelled receptor which specifically binds to complexes of analyte and labelled receptor but not to said inhibitor when liquid containing (a) complexes of analyte and labelled receptor and (b) inhibitor flow therein from said first zone, wherein said contacting is carried out under conditions favoring binding of said complex and said solid phase receptor, (iv) removing said inhibitor from said second zone, and (v) determining a detectable signal produced in said second zone by said label in said complex as a determination of said analyte.

12. Method of claim 1, wherein said analyte is contacted with a plurality of receptors one of which carries a label with an inhibitor specific for that label carried thereon.

13. Method of claim 12, wherein one of said plurality of receptors comprises a labeled Fab fragment.

14. Method of claim 12, wherein said plurality of receptors comprises monoclonal antibodies or fragments thereof.

15. Method of claim 11, wherein said first zone further comprises a second, non-solid phase bound unlabelled receptor which specifically binds to said analyte but not said unlabelled receptor, and said solid phase bound, unlabelled receptor specifically binds to said second, non solid phase bound, unlabelled receptor.

16. Method of claim 11, wherein said label is an enzyme.

17. Multizone test apparatus useful in determining an analyte in a liquid sample, said test apparatus comprising a first zone in fluid contact with a second zone, and a third zone in fluid contact with said second zone, wherein:

(i) said first zone contains at least one non-solid phase bound, label carrying receptor which specifically binds to said analyte, (ii) said second zone contains a non-solid phase bound inhibitor for the label of said unlabelled receptor, wherein said inhibitor is not acted upon by said label and directly inhibits said label from providing a detectable signal, and (iii) said third zone contains a solid phase bound, unlabelled receptor which specifically binds to a complex of said analyte and said first receptor.

18. Multizone test apparatus of claim 17, wherein said first zone further comprises a second, non-solid phase bound, unlabelled receptor which specifically binds to said analyte but not said labelled receptor, and said solid phase bound, unlabelled receptor binds to a complex of analyte, labelled receptor and unlabelled, non-solid phase bound receptor via said non-solid phase bound unlabelled receptor.

19. Multizone test apparatus of claim 17, further comprising a fourth zone positioned between said first zone and said second zone which contains a substrate which reacts with said label to form a detachable signal.

20. Multizone test apparatus of claim 17, wherein said label is an enzyme.

21. Multizone test apparatus useful in determining an analyte in a liquid sample, said test apparatus comprising a first zone in fluid contact with a second zone, wherein:

(i) said first zone contains both at least one non-solid phase bound, labelled receptor which specifically binds to said analyte, and (b) a non-solid phase bound inhibitor for the label of said labelled receptor, wherein said inhibitor is not acted upon by said label and directly inhibits said label from providing a detectable signal, and (ii) a second zone containing a solid phase bound, unlabelled receptor which specifically binds to a complex of said analyte and said labelled receptor.

22. Multizone test apparatus of claim 21, wherein said first zone also contains a non-solid phase bound, unlabelled receptor which specifically binds to said analyte but not said non-solid phase bound, labelled receptor, and said solid phase bound, unlabelled receptor binds to a complex of analyte, labelled receptors and non-solid phase bound, unlabelled receptor via said non-solid phase bound unlabelled receptor.

23. Multizone test apparatus of claim 21, further comprising a third zone positioned between said first zone and said second zone which contains a substrate which reacts with said label to form a detectable signal.

24. Multizone test apparatus of claim 21, wherein said label is an enzyme.

* * * * *